United States Patent [19]

Fahmy et al.

[11] 4,261,897

[45] Apr. 14, 1981

[54] N-CHLOROSULFINYLCARBAMATE ESTERS

[75] Inventors: Mohamed A. H. Fahmy; Tetsuo R. Fukuto, both of Riverside, Calif.

[73] Assignee: The Regents of the University of California, Los Angeles, Calif.

[21] Appl. No.: 18,416

[22] Filed: Mar. 7, 1979

[51] Int. Cl.³ .................. C07D 317/44; C07C 149/43; C07C 125/04; C07D 307/77

[52] U.S. Cl. ................ 260/340.5 R; 260/346.22; 260/464; 260/465 D; 260/465.4; 260/340.9 R; 560/10; 560/16; 560/115; 560/134; 560/135; 560/136; 560/137; 560/148

[58] Field of Search ........... 560/148, 16, 137, 134, 560/135, 136, 10, 115; 260/346.22, 340.5 R, 464, 465.4, 465 D; 424/300, 282, 285

[56] References Cited

U.S. PATENT DOCUMENTS

| | | | |
|---|---|---|---|
| 3,663,594 | 5/1972 | Brown et al. | 560/10 |
| 3,843,688 | 10/1974 | Cleveland | 260/346.73 |
| 3,843,689 | 10/1974 | Brown et al. | 560/135 |
| 3,914,259 | 10/1975 | Brown et al. | 560/136 |
| 3,950,374 | 4/1976 | Ueda et al. | 424/300 X |
| 3,969,407 | 7/1976 | Phillips et al. | 260/465 D |
| 4,138,423 | 2/1979 | D'Silva | 260/464 |

FOREIGN PATENT DOCUMENTS

| | | | |
|---|---|---|---|
| 1095806 | 6/1961 | Fed. Rep. of Germany | 560/137 |
| 2106300 | 8/1972 | Fed. Rep. of Germany | 424/300 |
| 49-25132 | 6/1974 | Japan | 424/300 |

*Primary Examiner*—Ethel G. Love
*Attorney, Agent, or Firm*—Herzig & Walsh, Inc.

[57] ABSTRACT

N-chlorosulfinylcarbamate esters are produced by the reaction of thionyl chloride with carbamate esters having one unsubstituted hydrogen on the carbamate nitrogen atom, preferably in the presence of a hydrogen chloride acceptor. The resulting N-chlorosulfinylcarbamate esters are useful intermediates in the preparation of pesticides having relatively low mammalian toxicity.

24 Claims, No Drawings

N-CHLOROSULFINYLCARBAMATE ESTERS

BACKGROUND OF THE INVENTION

This invention relates to the production of novel carbamate esters, and is particularly concerned with the production of novel carbamate esters useful as intermediates in the preparation of pesticides.

Pesticides derived from or in the form of carbamate esters are well known, as exemplified by U.S. Pat. Nos. 3,474,170 and 3,474,171 to Scharpf, and U.S. Pat. Nos. 3,997,549, 4,006,231, and 4,108,991, to Fukuto and Black.

U.S. Pat. No. 3,843,689 to Brown and Kohn discloses N-chlorothiocarbamates useful as intermediates in the preparation of carbamate ester pesticides.

It is an object of the present invention to provide another novel class of carbamate ester compounds useful as intermediates in the production of effective pesticides, and to provide novel procedure for preparing such compounds.

SUMMARY OF THE INVENTION

The novel carbamate ester compounds of the invention are N-chlorosulfinylcarbamate esters having the formula noted below, and are prepared by reacting thionyl chloride with carbamate esters either directly with heating, or in a suitable organic solvent with the aid of a hydrogen chloride acceptor such as pyridine.

DETAILED DESCRIPTION OF THE INVENTION AND PREFERRED EMBODIMENTS

The N-chlorosulfinylcarbamate esters of the invention have the formula noted below;

   (1)

wherein $R_1$ is selected from the group consisting of a hydrocarbyl group containing from 1 to 20 carbon atoms, a 5 to 6 membered heterocyclic ring containing O or S atoms, and the $>C=N-$ group, and $R_2$ is a hydrocarbyl group containing from 1 to 12 carbon atoms.

The compounds of formula (1) above are produced by reacting carbamate esters having one unsubstituted hydrogen on the carbamate nitrogen atom, with thionyl chloride according to the following general equation:

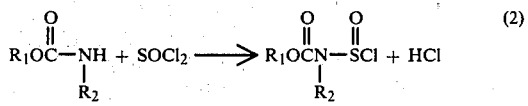   (2)

wherein:

$R_1$ can be a hydrocarbyl group containing only hydrogen and carbon, and containing from 1 to 20 carbon atoms, including substituted or unsubstituted alkyl, cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio and alkoxy groups; a 5 or 6 membered heterocyclic ring containing O or S atoms, e.g. benzothienyl, furanyl, benzofuranyl and 1,3-benzodioxolyl; or the $>C=N-$ group. The latter group can be represented by the formula:

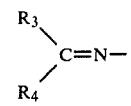

where $R_3$ is hydrogen, alkyl, alkylthio or cyano, and $R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where $R_1$ is aryl, preferred examples of such aryl groups are as follows:

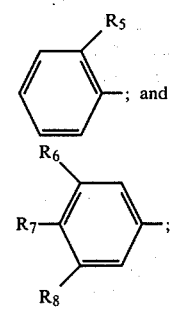

where $R_5$ is hydrogen, alkoxy, alkylthio, alkyl, alkylthioalkyl, 2-dioxolanyl dioxalanyl or halogen, e.g. Cl or Br;

$R_6$ is alkyl, alkoxy, alkoxyalkyl or halogen;

$R_7$ is hydrogen, alkyl, halogen, alkylthio, alkoxy or dialkylamino;

$R_8$ is hydrogen or alkyl; and wherein the number of aliphatic carbon atoms in $R_3$, $R_4$, $R_5$, $R_6$, $R_7$, and $R_8$, individually should not exceed eight; and $R_2$ is a hydrocarbyl group, either alkyl or aryl, e.g. a straight chain, branched or carbocyclic (five or six membered ring) alkyl, phenylalkyl or phenyl, and containing from 1 to 12 carbon atoms.

A preferred class of carbamate ester compounds of the invention are those wherein $R_1$ and $R_2$ are hydrocarbyl groups, each containing from 1 to 12 carbon atoms, either aliphatic or aromatic. These can include alkyl, e.g. methyl, ethyl, isopropyl, n-propyl, isobutyl, and the like, cycloalkyl, e.g. cyclohexyl, phenylalkyl, naphthylalkyl; aryl, e.g. phenyl, naphthyl, alkylphenyl and alkylnaphthyl, any of which can contain substituents such as dialkylamino, halogen, e.g. chlorine or bromine, alkoxy and alkylthio. Particularly preferred are those compounds where $R_1$ is alkyl, phenyl, phenylalkyl or naphthyl, and which can be unsubstituted or substituted, e.g. with halogen, alkoxy, dialkylamino groups, and the like, and $R_2$ is alkyl, and especially wherein $R_1$ is 3-alkylphenyl such as 3-isopropyl- and 3-secbutylphenyl, 2-alkoxyphenyl such as 2-isopropoxyphenyl, or 1-naphthyl, and wherein $R_2$ is alkyl, e.g. methyl. Particularly preferred also are those carbamate esters wherein $R_1$ is a heterocyclic ring, and including fused-on heterocyclic rings, containing one or two O or S atoms, and 5 to 6 members in the heterocyclic nucleus, e.g. benzothienyl, benzofuranyl, and especially a 2,3-dihydro-benzofuranyl-7 group having the formula (3) below, and the 1,3-benzodioxol-4-group having the formula (3a) below:

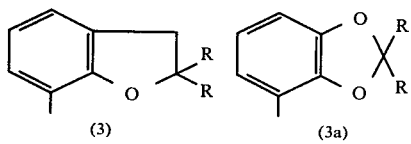

where R is an alkyl group of 1 to about 4 carbon atoms, e.g. methyl, ethyl, propyl, n-butyl, and both R's can be the same or different, and most preferably wherein $R_1$ is the 2,3-dihydro-2,2-dimethylbenzofuranyl-7 group; and $R_2$ is alkyl, e.g. methyl. Another particularly preferred class of carbamates of the invention are those wherein $R_1$ is the group containing the $>C=N-$ group or radical as defined above, and where $R_3$ is hydrogen, alkyl or alkylthio and $R_4$ is alkyl, alkylthio, alkoxy, dialkylaminocarbonyl or alkylthioalkyl; and $R_2$ is alkyl, e.g. methyl. Preferred $>C=N-$ groups are the following:

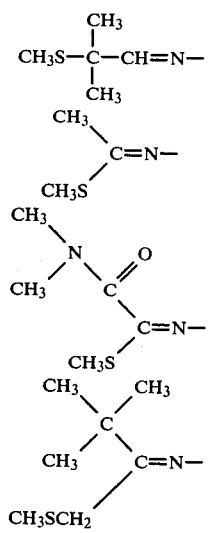

The carbamate esters of the invention and defined by formula (1) above, are prepared by reacting the carbamate starting materials with thionyl chloride, according to equation (2) above, directly with heating to form the corresponding N-chlorosulfinyl derivative and HCl. Such reaction is generally carried out at temperature ranging from about 60° to about 100° C., employing an excess of thionyl chloride of up to about 50% above the stoichiometric equivalent proportion with respect to the carbamate starting material which is required. HCl is evolved during the reaction and excess thionyl chloride is removed.

Alternatively, the reaction between the carbamate starting material and thionyl chloride can be carried out in a polar non-hydroxylic or non-polar organic solvent which will not react with thionyl chloride. Examples of suitable solvents are tetrahydrofuran, dichloromethane and hexane. An acid or hydrogen chloride acceptor is added to the solvent to aid the reaction. A preferred hydrogen chloride acceptor is pyridine. However other tertiary organic amines can be employed for this purpose including dimethyl- or diethylaniline, as well as pyridine. The reaction employing an organic solvent and hydrogen chloride acceptor can be carried out from room temperature up to an elevated temperature of about 60° C.

In the latter mode of reaction employing an organic solvent and HCl acceptor, essentially stoichiometric equivalent proportions of thionyl chloride are employed with respect to carbamate starting material. However, if desired a small excess of thionyl chloride up to about 10 mol% based on the carbamate can be employed. Approximately equivalent proportions of HCl acceptor, e.g. pyridine, with respect to carbamate starting material generally are employed. However, an excess of pyridine with respect to carbamate starting material also can be employed, e.g. up to about 25 mol%.

The latter mode of procedure is preferred and can be used for all carbamates. It is particularly useful for the preparation of N-chlorosulfinyl derivatives from carbamates that are susceptible to reaction with acids such as HCl, e.g. oxime carbamates such as aldicarb, which is 2-methyl-2-(methylthio)-propionaldehyde O-methylcarbamoyloxime, containing the oxime group shown in formula (4) above, and methomyl, which is S-methyl N-(methylcarbamoyloxy)thioacetimidate, containing the oxime group shown in formula (5) above.

The following are examples of preparation of N-chlorosulfinylcarbamate esters according to the invention.

EXAMPLE 1

Synthesis of isopropyl (chlorosulfinyl)(methyl)carbamate.

Forty grams of isopropyl methylcarbamate (0.34 mol) were mixed with 60 g thionyl chloride (0.5 mol) and stirred at room temperature for 1 hour. Then the temperature was raised to 60°–75° C. and heating was continued until HCl evolution ceased. Excess thionyl chloride was removed under water aspirator vacuum and the residue was distilled. The product distilled at 70° C./2.8 mm. The yield was 57 g (84% yield).

Analysis calculated for $C_5H_{10}NO_3SCl$, Carbon, 30.08%, Hydrogen, 5.01%. Found: Carbon, 30.51%, Hydrogen, 5.02%.

EXAMPLE 2

Synthesis of isopropyl (chlorosulfinyl)(phenyl)carbamate.

Eighteen grams isopropyl phenylcarbamate (~0.1 mol) and 14.0 g thionyl chloride (0.12 mol) were dissolved in 50 ml dry tetrahydrofuran and protected from moisture by a calcium chloride tube. Eight grams pyridine (0.1 mol) were added dropwise while the mixture was stirring at a water bath temperature (15°–20° C.). After the addition of pyridine was completed, the mixture was stirred for 12 hours at room temperature. Pyridine hydrochloride was filtered and the solvent was removed under vacuum. The concentrated residue was diluted with hexane and filtered. The hexane was removed under vacuum and the residue was distilled, giving 16.0 g of product distilling at 113–115/0.08 mm. NMR spectrum of the product in chloroform-d-TMS gave the following absorptions: $\delta 7.6$-7.2 (m, 5H, phenyl protons), $\delta 5.5$-4.9 (m, 1H, CH) and $\delta 1.4$-1.3 (d, 6H, $C(CH_3)_2$).

EXAMPLE 3

Synthesis of 3-isopropylphenyl (chlorosulfinyl)(methyl)carbamate.

Four grams 3-isopropylphenyl methylcarbamate were mixed with excess thionyl chloride and heated up to 80° C. until HCl evolution ceased. Excess thionyl chloride was removed by distillation and the residue was subjected to high vacuum (0.1 mm) for 1 hour. NMR of the residue in chloroform-d-TMS gave the following absorptions: $\delta 7.5$–6.9 (m, 4H, aromatic protons). $\delta 3.25$ (s, 3H, NCH$_3$), $\delta 3.2$–2.7 (m, 1H, CH), and $\delta 1.3$–1.2 (d, 6H, C(CH$_3$)$_2$).

EXAMPLE 4

Synthesis of 2,3-dihydro-2,2-dimethylbenzofuranyl-7 (chlorosulfinyl)(methyl)carbamate.

Five and one-half grams of carbofuran (2,3-dihydro-2,2-dimethylbenzofuranyl-7 methylcarbamate) (0.025 mol) were dissolved in 25 ml dry tetrahydrofuran. To this solution was added 2.5 g pyridine (0.032 mol) followed by 3.5 g thionyl chloride (0.03 mol). The mixture was stirred at room temperature for 6 hours, then filtered under nitrogen to remove pyridine hydrochloride. The solvent was evaporated under vacuum, and the viscous solution was subjected to high vacuum (0.05 mm) for 1 hour. NMR of the residue in chloroform-d-TMS showed the following absorptions: $\delta 7.3$–6.7 (m, 3H, aromatic protons), $\delta 3.25$ (s, 3H, NCH$_3$), $\delta 3.05$ (s, 2H, benzylic CH$_2$), $\delta 1.45$ (s, 6H, gem-diCH$_3$). The spectrum is consistent with the structure.

The following are examples of additional representative carbamate ester compounds according to the invention:

- Methyl (chlorosulfinyl)(methyl)carbamate
- Ethyl (chlorosulfinyl)(methyl)carbamate
- n-Butyl (chlorosulfinyl)(methyl)carbamate
- Cyclohexyl (chlorosulfinyl)(methyl)carbamate
- n-Propyl (chlorosulfinyl)(ethyl)carbamate
- 2,2,2-Trichloroethyl (chlorosulfinyl)(methyl)carbamate
- 3,4-Methylenedioxybenzyl (chlorosulfinyl)(methyl)carbamate
- 4-Chlorobenzyl (chlorosulfinyl)(methyl)carbamate
- Phenyl (chlorosulfinyl)(methyl)carbamate
- Phenyl (chlorosulfinyl)(ethyl)carbamate
- 3-sec-Butylphenyl (chlorosulfinyl)(methyl)carbamate
- 1-Naphthyl (chlorosulfinyl)(methyl)carbamate
- 2-Naphthyl (chlorosulfinyl)(ethyl)carbamate
- 2-Isopropoxyphenyl (chlorosulfinyl)(methyl)carbamate
- 2,4,5-Trimethylphenyl (chlorosulfinyl)(methyl)carbamate
- 3-Methyl-4-dimethylaminophenyl (chlorosulfinyl)(methyl)carbamate
- 2-Chlorophenyl (chlorosulfinyl)(methyl)carbamate
- 3,5-Diisopropylphenyl (chlorosulfinyl)(methyl)carbamate
- n-Propyl (chlorosulfinyl)(phenyl)carbamate
- S-Methyl N-[(chlorosulfinyl)(methyl)carbamoyloxy]thioacetimidate
- 2-Methyl-2-(methylthio)propionaldehyde O-[(chlorosulfinyl)(methyl)carbamoyl]oxime
- S-Methyl N',N'-dimethyl-N-(chlorosulfinyl)(methyl)carbamoyloxy-1-thio-oximidate
- 2,2-dimethyl-1,3-benzodioxoyl-4 (chlorosulfinyl)(methyl)carbamate

UTILITY

The N-chlorosulfinylcarbamates of the invention are useful effective intermediates for the preparation of pesticides. Thus, for example, the N-chlorosulfinylcarbamates of the invention can be prepared and reacted, either separately, or in situ, with nucleophiles such as alcohols, phenols, thiols, amines, carbamates, amides, sulfonamides, ureas, and sulfonyl ureas, and the like. The resulting products of the reaction are effective insecticides, nematicides, miticides, and herbicides, dependent upon the structure of the particular carbamate ester and the functional groups.

The following examples are illustrative of the conversion of the N-chlorosulfinylcarbamates of the invention to carbamate compounds useful as pesticides.

EXAMPLE 5

Preparation of 2,3-dihydro-2,2-dimethylbenzofuranyl-7 (methyl)(hexoxysulfinyl)carbamate.

A mixture of 2,3-dihydro-2,2-dimethylbenzofuranyl-7 methylcarbamate (5.5 g, 0.025 mol), pyridine (2.5 g, 0.032 mol), thionyl chloride (3.0 g., 0.025 mol), and 25 ml anhydrous tetrahydrofuran, was stirred at room temperature for 6 hours, Pyridine hydrochloride separates immediately after mixing, and continued stirring is to insure complete reaction. To this mixture was added 2 g pyridine (0.025 mol) followed by 3 g n-hexyl alcohol (0.029 mol) added dropwise. After stirring for an additional hour, 150 ml ether were added to the reaction mixture. The mixture was washed with water three (30 ml each) times. The ether solution was dried over anhydrous sodium sulfate, filtered and concentrated under vacuum. Unreacted carbamate (about 0.5 g) crystallized out and was filtered. The remaining liquid, 7.4 g was almost free from unreacted carbamate as evident from the NMR spectrum of this crude product.

A sample of this product was further purified by preparative thin layer chromatography using ether-hexane (3:1) mixture as the developing solvent, and NMR spectrum obtained.

Analysis calculated for $C_{18}H_{27}O_5NS$; Carbon, 58.51%, Hydrogen, 7.37%. Found: Carbon, 59.24%, Hydrogen 8.08%.

EXAMPLE 6

Preparation of 2,3-dihydro-2,2-dimethylbenzofuranyl-7 (methyl)(n-butylthiosulfinyl)carbamate.

To a solution of 4.4 g (0.02 mol) 2,3-dihydro-2,2-dimethylbenzofuranyl-7 methylcarbamate in 20 ml dry tetrahydrofuran was added 1.9 g (0.025 mol) pyridine followed by 2.5 g (0.021 mol) thionyl chloride. The mixture was stirred at room temperature for 4 hours. Pyridine (1.9 g, 0.025 mol) was added and the mixture was cooled in an ice-water bath. To this stirring solution was added, dropwise, 1-butanethiol (1.8 g 0.02 mol) in 2 ml tetrahydrofuran. After the complete addition of the thiol, the mixture was allowed to warm up to room temperature and kept at this temperature for ½ hour. Ether, 150 ml, was added to the mixture and washed four times (25 ml each) with water. The ether solution was dried over anhydrous sodium sulfate and the solvent was evaporated under vacuum. The residue was subjected to high vacuum (0.1 mm) for several hours. Nmr spectrum of this crude product showed a complete conversion of 2,3-dihydro-2,2-dimethylbenzofuranyl-7 methylcarbamate to its butylthiosulfinyl derivative.

Analysis calculated for $C_{16}H_{23}NO_4S_2$; carbon, 53.75%; hydrogen, 6.48%. Found: carbon, 53.97%; hydrogen 6.48%.

EXAMPLE 7

Synthesis of S-methyl N-[N'-(N''-ethyl-N''-n-propoxycarbonylaminosulfinyl)-N'-methylcarbamoyloxy]thioacetimidate.

To a solution of S-methyl N-(N'-methylcarbamoyloxy)thioacetimidate (3.3 g, 0.02 mol) in 20 ml anhydrous dichloromethane, was added 4.3 g of propyl (ethyl)(chlorosulfinyl)carbamate (prepared from propyl ethylcarbamate and thionyl chloride, B.p. 65°–69° C. at 0.5 mm) and 1.6 g (0.02 mol) anhydrous pyridine. The mixture was stirred for twelve hours at room temperature. Ether (100 ml) was added and the mixture was washed with water three (30 ml each) times. The ether solution was dried over anhydrous sodium sulfate, filtered and concentrated under vacuum. A sample of the oily residue was purified by preparative thin-layer chromatography using ether-hexane (3:1) mixture as the developing solvent, and the NMR spectrum obtained.

Analysis calculated for $C_{11}H_{21}N_3O_5S_2$; carbon, 38.92%; hydrogen, 6.23%. Found: carbon, 38.38%; hydrogen, 5.78%.

Each of the compounds of Examples 5, 6 and 7 above were tested for insecticidal activity by preparing an acetone solution of each of the three compounds, each solution containing a concentration of 0.1 g of the compound per liter. House flies were treated topically on the notum by 0.001 ml of each of the three acetone solutions and the % mortality in each case was counted 24 hours after application. A high mortality rate based on the above noted concentration of the acetone solution was obtained in each case.

Mammalian toxicity of each of the three compounds of Examples 5, 6 and 7 was determined against Swiss white mice. Each of the test compounds was applied orally using corn oil as the carrier. Results showed relatively low toxicity of each of the compounds to the mice.

It is noted in Examples 5 and 6 that the intermediates produced therein by the initial reaction with thionyl chloride according to the invention, were not isolated, but were reacted in situ with n-hexyl alcohol and 1-butanethiol, respectively. However, in Example 7 the chlorosulfinylcarbamate intermediate was first prepared, and isolated, and then reacted with the oxime carbamate reactant. The in situ reaction without isolation of the intermediate is particularly convenient for producing the desired insecticide. This is especially the case in certain instances where the intermediate is relatively difficult to purify by distillation or any other conventional method of purification.

From the foregoing, it is seen that the invention provides novel N-chlorosulfinylcarbamate esters by relatively simple procedure of reacting suitable carbamates with thionyl chloride, the resulting compounds being useful intermediates for the preparation of effective pesticides having low mammalian toxicity.

While we have described particular embodiments of the invention for purposes of illustration, it will be understood that various changes and modifications within the spirit of the invention can be made, and the invention is not to be taken as limited except by the scope of the appended claims.

What is claimed is:

1. N-chlorosulfinylcarbamates having the formula:

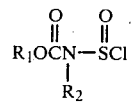

wherein $R_1$ is selected from the group consisting of a hydrocarbyl group containing from 1 to 20 carbon atoms, a 5 to 6 membered heterocyclic ring consisting essentially of one to two O or S atoms, the remaining ring atoms being carbon atoms, and the $>C=N-$ group,

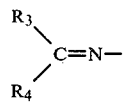

where $R_3$ is a hydrogen, alkyl, alkylthio, or cyano; and $R_4$ is alkyl, alkylthio, alkoxy, alkanoyl, alkoxycarbonyl, dialkylaminocarbonyl, phenyl, and which can be unsubstituted or substituted with one or more cyano, nitro, alkylthio, alkylsulfinyl, alkylsulfonyl or alkoxy groups; the number of aliphatic carbon atoms in $R_3$ and $R_4$, individually, not exceeding eight, and $R_2$ is a hydrocarbyl group containing from 1 to 12 carbon atoms.

2. Carbamates as defined in claim 1, wherein $R_1$ is an aryl group selected from the class consisting of:

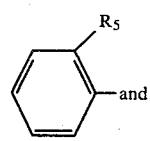

where $R_5$ is hydrogen, alkoxy, alkylthio, alkyl, alkylthioalkyl, 2-dioxolanyl, or halogen;
$R_6$ is alkyl, alkoxy, alkoxyalkyl, or halogen;
$R_7$ is hydrogen, alkyl, halogen, alkylthio, alkoxy or dialkylamino; and
$R_8$ is hydrogen or alkyl; the number of aliphatic carbon atoms in $R_5$, $R_6$, $R_7$, and $R_8$, individually, not exceeding eight.

3. Carbamates as defined in claim 1, wherein $R_2$ is selected from the group consisting of straight chain, branched and carbocyclic (five or six membered ring) alkyl, phenylalkyl and phenyl.

4. Carbamates as defined in claim 2, wherein $R_1$ is:

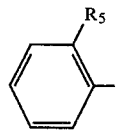

5. Carbamates are defined in claim 2, wherein $R_1$ is:

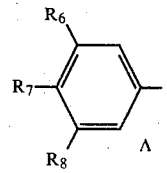

6. N-chlorosulfinylcarbamates having the formula:

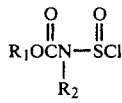

wherein $R_1$ is selected from the group consisting of substituted and unsubstituted alkyl, cycloalkyl, phenylalkyl and naphthylalkyl, and substituted and unsubstituted phenyl and naphthyl, and wherein the aforementioned groups can be substituted with a member selected from the group consisting of one or more halogen, cyano, nitro, alkyl, alkylthio and alkoxy groups; a heterocyclic ring consisting essentially of one or two O or S atoms, the remaining ring atoms being carbon atoms, and 5 to 6 members in the heterocyclic nucleus; and the >C=N— group,

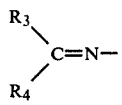

where $R_3$ is a hydrogen, alkyl, alkylthio, or cyano; and $R_4$ is alkyl, alkylthio, alkoxy, alkanoyl, alkoxycarbonyl, dialkylaminocarbonyl, phenyl, and which can be unsubstituted or substituted with one or more cyano, nitro, alkylthio, alkylsulfinyl, alkylsulfonyl or alkoxy groups; the number of aliphatic carbon atoms in $R_3$ and $R_4$, individually, not exceeding eight, and $R_2$ is selected from the group consisting of straight chain, branched and carbocyclic (five or six membered ring) alkyl, phenylalkyl and phenyl, and $R_1$ and $R_2$ each contains from 1 to 12 carbon atoms.

7. Carbamates as defined in claim 6, wherein $R_1$ is selected from the group consisting of alkyl, phenyl, phenylalkyl and naphthyl, and $R_2$ is alkyl.

8. Carbamates as defined in claim 7, wherein $R_1$ is selected from the group consisting of 3-alkylphenyl, 2-alkoxyphenyl and 1-naphthyl groups.

9. Carbamates as defined in claim 7, wherein $R_1$ is selected from the group consisting of 3-isopropyl and 3-secbutylphenyl, 2-isopropoxyphenyl and 1-naphthyl groups and $R_2$ is methyl.

10. Carbamates as defined in claim 6, wherein $R_1$ is a heterocyclic or fused-on heterocyclic ring containing one or two O or S atoms, the remaining ring atoms being carbon atoms, and 5 to 6 members in the heterocyclic nucleus, and $R_2$ is alkyl.

11. Carbamates as defined in claim 10, wherein $R_1$ is a benzofuranyl group or, a 1,3-benzodioxolyl group.

12. Carbamates as defined in claim 10, wherein $R_1$ is selected from the class having the formulae:

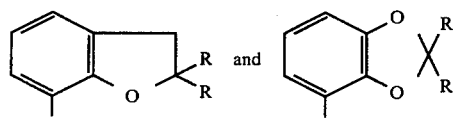

where R is an alkyl group of 1 to about 4 carbon atoms, and both R's can be the same or different.

13. Carbamates as defined in claim 10, wherein $R_1$ is the 2,3-dihydro-2,2-dimethylbenzofuranyl-7 group.

14. Carbamate as defined in claim 10, wherein $R_1$ is the 2,3-dihydro-2,2-dimethylbenzofuranyl-7 group, and $R_2$ is methyl.

15. Carbamate as defined in claim 10, wherein $R_1$ is the 1,3-benzodioxol-4 group.

16. Carbamate as defined in claim 10, wherein $R_1$ is the 2,2-dimethyl 1,3-benzodioxol-4 group, and $R_2$ is methyl.

17. N-chlorosulfinylcarbamates having the formula:

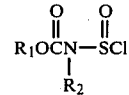

wherein $R_1$ is a group selected from the class consisting of those having the formulae:

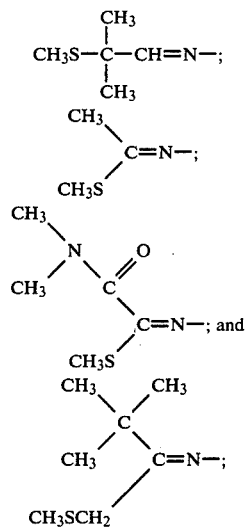

and $R_2$ is alkyl.

18. Carbamates as defined in claim 17, wherein $R_2$ is methyl.

19. Carbamate as defined in claim 17, wherein $R_1$ is the group having the formula:

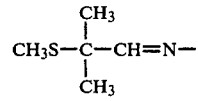

and $R_2$ is methyl.

20. Carbamate as defined in claim 1, which is isopropyl (chlorosulfinyl)(methyl)carbamate.

21. Carbamate as defined in claim 1, which is 3-isopropylphenyl (chlorosulfinyl)(methyl)carbamate.

22. Carbamate as defined in claim 1, which is 2,3-dihydro-2,2-dimethylbenzofuranyl-7 (chlorosulfinyl)(methyl) carbamate.

23. Carbamate as defined in claim 1, которое is 1-Naphthyl (chlorosulfinyl)(methyl)carbamate.

24. S-Methyl N-[(chlorosulfinyl)(methyl)carbamoyloxy]thioacetimidate.

* * * * *